US012318218B1

(12) United States Patent
Roy et al.

(10) Patent No.: US 12,318,218 B1
(45) Date of Patent: *Jun. 3, 2025

(54) VIRTUAL HEALTH COACH FOR FACILITATING DYNAMIC DOSAGE TITRATION

(71) Applicant: Verily Life Sciences LLC, Mountain View, CA (US)

(72) Inventors: Nikhil Roy, Sunnyvale, CA (US); Miguel Angelo Drumond, Oakland, CA (US)

(73) Assignee: Verily Life Sciences LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/649,589

(22) Filed: Apr. 29, 2024

Related U.S. Application Data

(63) Continuation of application No. 17/933,540, filed on Sep. 20, 2022, now Pat. No. 12,023,175, which is a
(Continued)

(51) Int. Cl.
*G16H 20/17* (2018.01)
*A61B 5/00* (2006.01)
(Continued)

(52) U.S. Cl.
CPC ............ *A61B 5/486* (2013.01); *A61B 5/0022* (2013.01); *A61B 5/0077* (2013.01); *A61B 5/1112* (2013.01); *A61B 5/1118* (2013.01); *A61B 5/14532* (2013.01); *A61B 5/4839* (2013.01); *G06F 40/30* (2020.01); *G06V 10/768* (2022.01); *G16H 20/10* (2018.01); *G16H 20/17* (2018.01);
(Continued)

(58) Field of Classification Search
CPC .................. G06Q 50/22–24; G16H 20/17
See application file for complete search history.

(56) References Cited

U.S. PATENT DOCUMENTS

| 5,997,485 A | 12/1999 | Ahmadzadeh |
| 2006/0047192 A1 | 3/2006 | Hellwig et al. |

(Continued)

FOREIGN PATENT DOCUMENTS

| KR | 20190036967 | * | 4/2019 | ............ G06Q 50/22 |
| KR | 20190036967 A | | 4/2019 | |

OTHER PUBLICATIONS

Designing a Chatbot for Diabetic Patients; Lokeman et al.; Aug. 2007 (Year: 2007).*
(Continued)

*Primary Examiner* — John A Pauls
(74) *Attorney, Agent, or Firm* — Perkins Coie LLP

(57) ABSTRACT

A computer-implemented method improves efficacy of diabetes self-management to obtain a measurement message and/or contextual activity information used to determine a suitable insulin dosage to treat a patient. The method includes simulating a health coach in a natural conversation to obtain a measurement of the patient's blood-glucose level, processing the measured blood-glucose level with a personalized insulin titration algorithm to determine an insulin dosage recommendation, and generating an electronic signal configured to cause a corresponding action to be performed by a computing device.

20 Claims, 7 Drawing Sheets

Related U.S. Application Data continuation of application No. 16/172,180, filed on Oct. 26, 2018, now Pat. No. 11,457,863.

(60) Provisional application No. 62/578,150, filed on Oct. 27, 2017.

(51) Int. Cl.

| | | |
|---|---|---|
| *A61B 5/11* | (2006.01) | |
| *A61B 5/145* | (2006.01) | |
| *G06F 40/30* | (2020.01) | |
| *G06V 10/70* | (2022.01) | |
| *G16H 20/10* | (2018.01) | |
| *H04L 51/02* | (2022.01) | |
| *G06Q 50/00* | (2012.01) | |
| *H04W 88/02* | (2009.01) | |

(52) U.S. Cl.
CPC .............. *H04L 51/02* (2013.01); *G06Q 50/01* (2013.01); *H04W 88/02* (2013.01)

(56) References Cited

U.S. PATENT DOCUMENTS

| | | | |
|---|---|---|---|
| 2007/0179434 A1* | 8/2007 | Weinert | G16H 20/10 604/66 |
| 2008/0086522 A1* | 4/2008 | Biggs | H04L 63/0245 709/202 |
| 2008/0201325 A1 | 8/2008 | Doniger et al. | |
| 2010/0331652 A1* | 12/2010 | Groll | A61B 5/7445 600/365 |
| 2011/0015511 A1 | 1/2011 | Bousamra et al. | |
| 2011/0119081 A1 | 5/2011 | Vespasiani | |
| 2012/0116196 A1 | 5/2012 | Tubb | |
| 2015/0120317 A1* | 4/2015 | Mayou | A61B 5/14552 705/2 |
| 2017/0004260 A1* | 1/2017 | Moturu | G16H 50/20 |
| 2017/0213009 A1 | 7/2017 | Tubb | |
| 2017/0329917 A1* | 11/2017 | McRaith | G16H 10/60 |
| 2018/0122363 A1* | 5/2018 | Braz | G10L 13/08 |
| 2018/0150524 A1* | 5/2018 | Anger | G06F 16/9535 |
| 2018/0315499 A1* | 11/2018 | Appelbaum | G16H 10/20 |
| 2019/0214124 A1 | 7/2019 | Mougiakakou et al. | |
| 2021/0241905 A1 | 8/2021 | Hoar et al. | |

OTHER PUBLICATIONS

Hoskins, Mike, "", https://www.healthline.com/diabetesmine/insulin-titration-apps#1, Mar. 20, 2017, 7.

Kennedy, Lynn, et al., "FDA Clears "My dose Coach" App to Optimize Basal Insulin Dosing", https://diatribe.org/fda-clears-my-dose-coach-app-to-optimize-basal-insulin-dosing, 2.

Lokman, Abbas Saliimi, et al., "Designing a Chatbot for Diabetic Patients", Universiti Malaysia Pahang; https://www.researchgate.net/publication/266872926; Aug. 2007.

* cited by examiner

VIRTUAL HEALTH COACH FOR FACILITATING DYNAMIC DOSAGE TITRATION

CROSS-REFERENCE TO RELATED APPLICATION

This application is a continuation of U.S. patent application Ser. No. 17/933,540, titled "Virtual Health Coach Based Insulin Titration Platform," filed Sep. 20, 2022, which is a continuation of U.S. patent application Ser. No. 16/172,180, tilted "Virtual Health Coach Based Insulin Titration Platform," filed Oct. 26, 2018, now U.S. Pat. No. 11,457,863, issued Oct. 4, 2022, which claims priority to U.S. Provisional Patent Application No. 62/578,150, titled "Virtual Health Coach Based Insulin Titration Platform," filed Oct. 27, 2017, each of which is incorporated by reference herein in its entirety.

TECHNICAL FIELD

The disclosed teachings relate to techniques for diabetes self-management. The disclosed teachings more particularly relate to automated techniques that improve user engagement to reliably obtain measurements and/or contextual information for insulin titration processes.

BACKGROUND

Insulin therapy is recommended under certain circumstances for patients with diabetes. Insulin therapy may be prescribed by a doctor for a patient to augment or replace the patient's malfunctioning physiology. The amount of insulin prescribed to a patient is a function of factors such as the patient's weight.

A doctor considers numerous factors when formulating a personalized diabetes management program for a patient. For example, blood-glucose levels, adverse effects of insulin, cost, likelihood of patient adherence, and quality of life may be factors considered when choosing a therapy for a patient. Augmentation therapy can include basal or bolus insulin. When using replacement therapy, about half of the total daily insulin dose is given as basal and the other half as bolus, divided up before breakfast, lunch, and dinner. Hence, replacement therapy includes basal-bolus insulin and correction or premixed insulin.

Titration of insulin over time is critical to improving glycemic control and preventing diabetes-related complications. Titration refers to determining a suitable insulin dosage amount to control a diabetic patient's symptoms while mitigating side effects. A patient typically works with the patient's doctor to determine a suitable dose of insulin. In one example, insulin should be titrated to achieve a target fasting blood-glucose level of 4.0 to 7.0 mmol/L. Individuals can be taught self-titration, or titration may be done in conjunction with a healthcare provider such as a doctor. A suggested starting dose of insulin may be 10 units once daily at bedtime. A suggested titration may be 1 unit per day until a target amount is reached.

Given the need for consistent and accurate treatment of diabetes, effective insulin titration is critically important to managing diabetes. Existing titration techniques typically require a healthcare provider to prepare a personalized schedule for measuring blood-glucose and for insulin titration to optimize insulin dosages as a function of measured blood-glucose levels. As such, a patient must follow a strict schedule to manage his or her diabetes, which is tedious and burdensome. As a result, a patient is likely to mismanage his or her diabetes and risks experiencing diabetes-related complications.

BRIEF DESCRIPTION OF THE DRAWINGS

Various features and characteristics of the disclosed technology will become more apparent to those skilled in the art from a study of the Detailed Description in conjunction with the drawings. Embodiments of the disclosed technology are illustrated by way of example and not limitation in the drawings, in which like references indicate similar elements.

Figure 1:
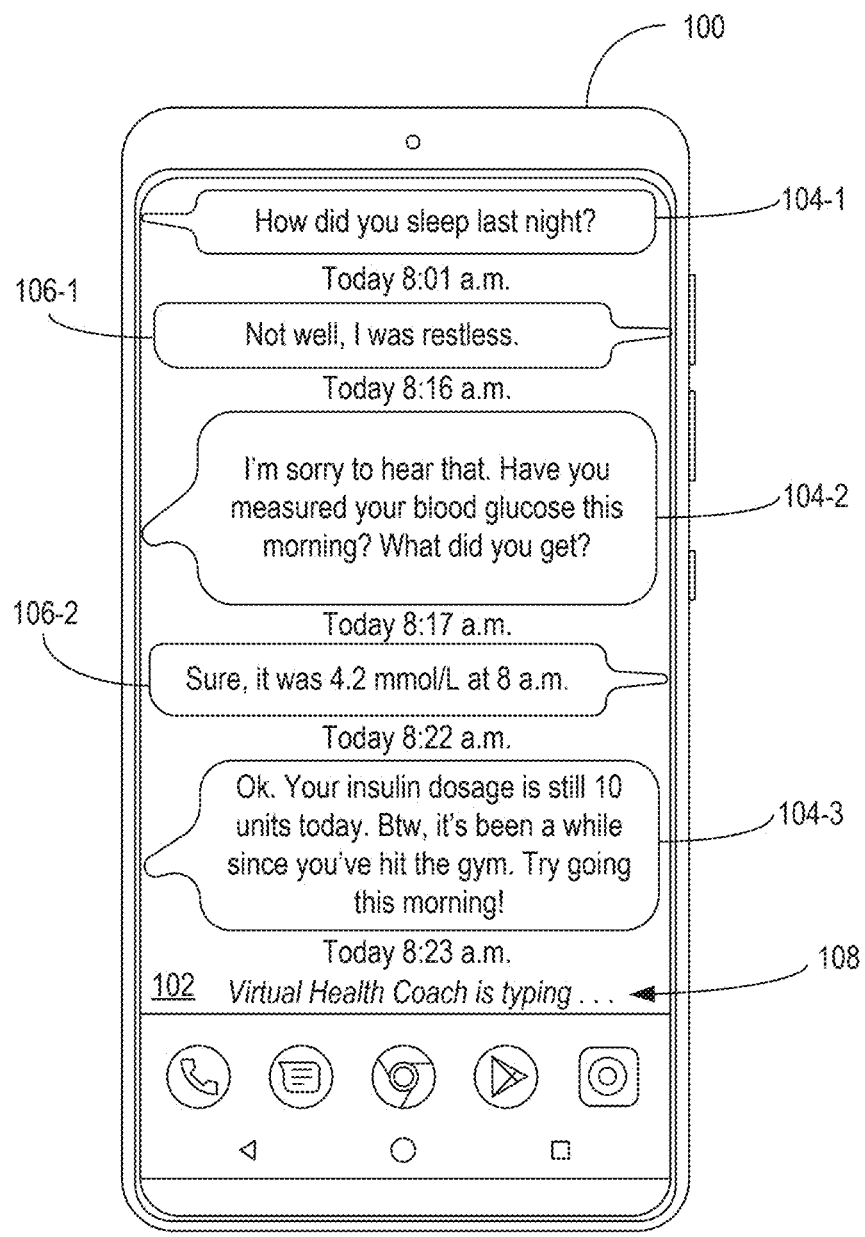
FIG. 1 illustrates a messaging interface displaying a natural conversation on a computing device between a user of the client device and a virtual health coach according to some embodiments of the present disclosure.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

The embodiments set forth below represent necessary information to enable those skilled in the art to practice the embodiments and illustrate the best mode of practicing the embodiments. Upon reading the following description in light of the accompanying Figures, those skilled in the art will understand the concepts of the disclosure and will recognize applications of these concepts that are not particularly addressed herein. It should be understood that these concepts and applications fall within the scope of the disclosure and the accompanying claims.

The purpose of the terminology used herein is only for describing embodiments and is not intended to limit the scope of the disclosure.

Reference to "one embodiment" or "an embodiment" means that a particular feature, structure, or characteristic described in connection with the embodiment is included in at least one embodiment of the disclosure. The appearances of the phrase "in one embodiment" in this disclosure are not necessarily all referring to the same embodiment, nor are separate or alternative embodiments necessarily mutually exclusive of other embodiments. Moreover, various features are described that may be exhibited by some embodiments and not by others. Similarly, various requirements are described that may be requirements for some embodiments and not for other embodiments.

As used herein, unless specifically stated otherwise, terms such as "processing," "computing," "calculating," "determining," "displaying," "generating," or the like, refer to actions or processes of an electronic device that manipulates and transforms data, represented as physical (electronic) quantities within the computer's memory or registers, into other data similarly represented as physical quantities within the device's memory, registers, or other such storage medium, transmission, or display devices.

When used in reference to a list of multiple items, the word "or" is intended to cover all of the following interpretations: any of the items in the list, all of the items in the list, and any combination of items in the list.

Unless the context clearly requires otherwise, throughout the description and the embodiments, the words "comprise," "comprising," and the like are to be construed in an inclusive sense, as opposed to an exclusive or exhaustive sense; that is to say, in the sense of "including, but not limited to."

As used herein, the terms "connected," "coupled," or any variant thereof, means any connection or coupling, either direct or indirect, between two or more elements; the coupling of or connection between the elements can be physical, logical, or a combination thereof. For example, two components may be coupled directly to one another or via one or more intermediary channels or components. As another example, devices may be coupled in such a way that information can be passed there-between, while not sharing any physical connection with one another. Where context permits, words in the Detailed Description using the singular or plural form may also include the plural or singular form, respectively.

A diabetes management plan includes an insulin titration process that is typically personalized for a patient by the patient's healthcare provider based on an assessment of various factors considered by the healthcare provider. For example, a doctor can administer an A1C test and/or determine a running average of blood-glucose levels by measuring fasting blood-glucose levels. In combination with other indicators, the healthcare provider can formulate a diabetes management plan for a patient.

For example, a diabetes management plan personalized for the patient can prescribe a certain basal insulin amount (e.g., 10 units) and instruct the patient to measure fasting blood-glucose levels daily. If a measured blood-glucose level is greater than a threshold amount, the user is instructed to increase an insulin dosage by some amount. Once the doctor has formulated a personalized diabetes management plan, the patient is given a pamphlet with related information and instructions for following the plan, including a prescription for increasing an insulin dosage amount as a function of blood-glucose levels.

In practice, a typical diabetes management plan involves escalating a patient through varying amounts of oral medication and then prescribing insulin treatments. The initial insulin treatments are basal amounts that are titrated up with the active assistance of a healthcare provider. For example, basal insulin amounts are increased with each visit by the patient to his or her doctor (e.g., about once every three months). Once a maximum amount of basal insulin has been prescribed to a patient, the healthcare provider then incorporates a bolus insulin treatment as part of the diabetes management plan.

Basal-based titration is a technique for determining an amount of first-line insulin that is long acting to lower a patient's baseline blood-glucose levels. In contrast, bolus-based titration is a technique for determining an amount of insulin that is rapid acting to counteract the effects of ingested carbohydrates. As such, bolus-based insulin is typically referred to a "mealtime insulin" because it is taken with meals to control the effect of the meals in real time. Eventually patients are prescribed bolus insulin, which is more complicated to formulate a suitable dosage amount because it requires an accurate estimation of carbohydrates ingested by the patient to counteract the body's response in real time with the bolus insulin. The fast acting nature of bolus insulin is typically too dangerous for self-management.

Given the burdensome nature of basal-based titration, which increases the risk that patients will simply quit self-managing, self-management plans that employ bolus or basal-bolus techniques are unlikely because the health consequences of non-adherence with these therapies is substantially more dangerous. Specifically, bolus-based titration is exceedingly complex because it requires considering numerous factors to formulate a suitable bolus dosage amount of insulin. For example, determining a bolus amount of insulin requires determining an insulin-to-carbohydrates ratio, to determine an expected insulin dosage amount that can counteract the effects of ingested carbohydrates. This can require a patient to engage in "carb counting," which is relatively difficult and burdensome to accurately measure routinely.

The risks of over-determining or under-determining ingested carbohydrates could be dire. For example, consequences include the patient experiencing a hyperglycemic event (i.e., patient has dangerously low blood sugar), which could result in coma or even death. Thus, diabetes self-management plans that include a manual insulin titration techniques are ineffective and have limited use because they are burdensome and the risks of mismanagement outweigh potential benefits.

Solutions to existing manual self-service diabetes management plans include computer-implemented diabetes management software programs that can aid a patient to manage his or her diabetes. Such computer-implemented techniques are generally based on basal insulin, and avoid the complexity and risks of basal-bolus insulin or bolus-based insulin. For example, a mobile application ("app") can facilitate basal-based titration for self-management of diabetes by the patient.

The diabetes management app can run on mobile devices such as smartphones, tablet computers, or wearable devices. In operation, the app has a user interface (UI) for a user to enter certain inputs. The user inputs are parsed and applied to one or more rules to recommend a dosage amount or an adjustment to a dosage amount. The UI is a basic interface that accepts data that is processed and presents results as outputs. The effectiveness of the app depends entirely on a patient's willingness to voluntarily provide inputs such as fasting blood-glucose levels measured by the patient daily. Hence, the app requires unnatural interactions by users to manage their diabetes. This process is so tedious and burdensome that patients eventually fail to correctly manage their diabetes.

Solutions to the shortcomings of existing computer-implemented techniques include significant engagement by the patient's healthcare provider in addition to engagement by the patient. That is, diabetes management typically has a limited self-management component and instead relies heavily on engagement by healthcare providers or third parties. Because typical healthcare providers cannot monitor all their patients to a degree required to adhere to diabetes management protocols, many patients simply quit and eventually suffer health consequences for their lack of adherence. As a result, engagement by healthcare providers with daily monitoring of patient diabetes management is negligible, especially after participating in the personalization of an algorithm for a particular patient. Instead, for example, the healthcare providers may generally engage diabetes management programs on limited occasions to correct mismanagement by their patients.

Diabetes management programs that include a self-management component have computer implemented algorithms. For example, a semi-automated mobile app can incorporate an algorithmic decision tree for basal insulin titration so that a healthcare provider can deliver whatever rules are necessary to aid the user. For example, a doctor can set a rule to increase an insulin dosage by 1 unit for every time the measure blood-glucose level of a patient exceeds a threshold amount. When a user inputs a measured blood-glucose level, the rules are applied to formulate a personalized output.

In fact, many insulin titration processes can be reduced to a number of rules of an algorithm executed by a computing device to aid the patient in self-managing diabetes. The personalized rules may include, for example, threshold values or conditions that are applied to inputs received from the patient including measurements of blood-glucose levels, and outputs are generated to instruct the user of the amount of insulin that should be consumed by the patient to maintain a healthy basal level of blood-glucose.

In many instances, different healthcare providers will adjust a set of rules based on different strategies and/or customize a set of rules of an insulin titration process for different patients as a function of different circumstances or factors that affect a patient. For example, different rules could be selected for different patients by type, including higher risk types that would be prescribed less aggressive therapy, and lower risk types that would be prescribed more aggressive therapy. As a result, an insulin titration process is personalized for each patient so that a recommended insulin amount will only be increased when needed for that particular patient.

It is not uncommon for a patient to eventually be prescribed a maximum amount of basal insulin because they failed to adhere to the diabetes management program. That is, patients fail to control their blood-glucose levels with adequate management such that the amount of insulin for a patient keeps getting incremented up. Other factors that contribute to this phenomena include the patient's insulin resistance or pancreatic function that lead to a growing need for more insulin. This phenomena is sometimes referred to as "chasing," which contributes to escalating fear by patients that they would need to continually increase their dosage and adds to a misperceived complexity of diabetes management. In some cases, users stagnate at a level due to this misplaced fear and never fully manage their diabetes such that their dosage levels are substantially increased overtime. As a result, any computer implemented insulin titration programs that could enable better self-management by users in an automated or semi-automated manner are disfavored as ineffective.

Ultimately, patients using a diabetes management program that involves a relatively greater self-management component fail. That is, the more that a patient is left to self-manage his or her diabetes, the greater the risk that the patient will fail to manage his or her diabetes because it is simply too easy for a user to quit the program.

The disclosed technology solves many of the aforementioned problems by employing effective self-service mechanisms for patients to manage their diabetes. In particular, the disclosed computer-implemented technology for managing diabetes involves insulin titration processes used to determine a suitable insulin dosage amount of insulin for a particular user. The disclosed technology can implement diverse types of insulin therapies including basal, basal-bolus, and bolus therapies.

Embodiments include a mobile app for self-managing diabetes by a patient. The technology deploys an insulin titration algorithm through a chat bot implemented as a virtual or simulated coach. Virtual health coaching involves the use of an automated communication device or service such as a chat bot that can engage a patient with a simulated natural conversation via a messaging mechanism of a mobile portal or web-based portal on a routine or regular basis.

In some embodiments, the virtual health coach can also run A/B testing and/or other dosage experimentation to help improve the simulated conversations or titration processes. For example, the virtual health coach can begin the titration process by asking a patient to fast or refrain from glucose for a day or two, and then begin suggesting different dosages on the following days.

In some embodiments, the virtual health coach can collect contextual information including patient activity (e.g., metabolic activity/exercise or taking of medication, eating of particular diet, real-time health/activity state from mobile/wearable sensors, self-reported health/activity state), external factors (e.g., longer day light, average temperature, season, geographical altitude, pollution level, environmental state from mobile/wearable sensors), or patient profile information (e.g., age, gender, genotype or phenotype information) to improve an insulin titration algorithm or adjust determined results.

The virtual health coach may be part of an insulin titration algorithm executing on a virtual health coach platform. The platform can include a combination of components such as the mobile app for managing diabetes. For example, the disclosed technology can include one or more algorithms deployed by the platform on a computing device that is local or remote from a device that received inputs of the patient. The insulin titration process is improved with the virtual health coach. By incorporating a virtual health coach into diabetes management, a patient is more engaged in his or her diabetes management because he or she enjoys the simulated natural conversations with the virtual health coach, which increases the likelihood that the patient will adhere to the diabetes management program that is otherwise complex and burdensome.

As used herein, a "virtual health coach" refers to a computer-implemented technique for automating health coaching processes via a computing device that encourages a user of the computing device to adhere to a given protocol in order to achieve a goal of that protocol. In one example, a virtual health coach is an implementation of a chat bot or other automated communications mechanism or device that can communicate with a patient via a local or network portal. For example, a virtual health coach could be part of a cloud service that communicates with a user on a daily basis via a mobile app resident on the user's smartphone or via a web-based portal linked to the cloud.

In some embodiments, a virtual health coach could be completely automated to function like a human being. As such, the user of a computing device can engage in a simulated natural conversation with a chat bot. In some embodiments, the virtual health coach operates in accordance with a set of rules that are customized for a particular user, a particular type of user, a group of users, etc. As such, the virtual health coach can be personalized. For example, a doctor could set rules or conditions executed by the virtual health coach to manage a patient's diabetes. In another example, a virtual health coach could be partially automated such that a third-party could influence the way a virtual health coach operates in real-time while engaged with a user.

As used herein, a "user" refers to an individual or entity that interacts with a virtual health coach via a computing device. Specifically, the user engages in a simulated conversation with a chat bot of a virtual health coach service. The user is typically the diabetic patient that is self-managing his or her diabetes with the virtual health coach service. In another example, a user could be a third party that enters inputs on behalf of the patient. In another example, the user is a healthcare provider that interacts with the virtual health coach platform to personalize the behavior of the chat bot for the user by adjusting rules, criteria, conditions, thresholds, other parameters, or combinations thereof.

In another example, a user could be an administrator of a virtual health coach platform that manages operations of its services. In yet another example, a user could be a computing device that interacts with the virtual health coach platform to aid the diabetic patient to manage his or her diabetes. As such, the user could be a device that provides feedback to a virtual health coach platform on behalf of the diabetic patient to manage his or her diabetes.

The disclosed technology overcomes drawbacks of existing insulin titration techniques by employing computer implemented processes that engage users in self-management of their diabetes in a manner that seems natural to a user through automated or semi-automated exchanges between the user and the virtual health coach, which can ultimately improve the effectiveness of the diabetes management programs by keeping the users highly engaged in their self-management. The use of a natural dialog can also expand the scope of information used to identify data points that can be analyzed to improve an insulin titration algorithm.

The virtual health coach is implemented with a messaging mechanism (rather than a UI) to improve engagement by a user with an insulin titration program. Examples of a virtual health coach include a chat messenger, SMS text, or other input mechanisms that can use a chat bot implemented as a virtual health coach to increase engagement by users with their diabetes management programs. Unlike techniques that use a UI for receiving inputs and presenting results as outputs calculated based on the inputs, the disclosed messaging mechanism is used to create a natural dialog that improves the likelihood that a user will engage with the virtual health coach. In some embodiments, a virtual health coach can routinely notify a patient to query the patient for input values such as measured blood-glucose levels. In other embodiments, the virtual health coach can engage a user in a natural conversation to extract the measured blood-glucose levels as well as other relevant information in a manner that is more engaging to that particular user.

FIG. 1 illustrates a natural conversation between a patient using a client device and a virtual health coach according to some embodiments of the present disclosure. The simulated natural conversation can engage a patient in a manner that effectively extracts user inputs necessary to perform insulin titration for a patient and, in some instances, derive related contextual information from the simulated conversation. The user inputs and/or contextual information can be used to improve the accuracy of a recommended insulin dosage amount.

As shown in FIG. 1, the computing device 100 is embodied as a smartphone that displays a messaging portal 102 that includes comments from the chat bot 104 and the patient 106 of a simulated natural conversation. Although embodied on a smartphone, the messaging portal 102 can run on any computing device or platform that allows the user to engage in a simulated natural conversation. For example, the messaging portal can be included in an app or be part of an operating system (OS) of a smartphone or other computing device. The messaging portal can receive messages from the virtual health coach that prompt the patient for user inputs required to perform insulin titration.

For example, the virtual health coach can send messages to a patient on a daily basis to engage in a brief simulated natural conversation meant to extract certain user inputs. In some embodiments, the simulated natural conversations may vary based on current events and/or events related to the patient's activities. By engaging a patient in simulated conversations in the context of current issues, the patient is more likely to remain interested in a simulated conversation.

For example, the simulated conversation illustrated on the messaging portal 102 of FIG. 1 engages the patient in the following dialog, which relates to how the patient slept the night before:

Virtual Health Coach: "How did you sleep last night?" (104-1)
Patient: "Not well, I was restless." (106-1)
Virtual Health Coach: "I'm sorry to hear that. Have you measured your blood-glucose this morning?What did you get?" (104-2)
Patient: "Sure, it was 4.2 mmol/L at 8 a.m." (106-2)
Virtual Health Coach: "Ok. Your insulin dosage is still 10 units today. Btw, it's been a while since you've hit the gym. Try going this morning!" (104-3)

In this example, the simulated conversation prompts the user for information necessary to perform insulin titration processes in the context of how the user's sleeping habits and prior activities. In some embodiments, the simulated conversation can vary the frequency, content, and tone of the messages as needed to achieve desired levels of engagement. In particular, the virtual health coach is trained with an expert knowledgebase encompassing diabetes, insulin titration techniques, and/or a variety of ways to engage users in simulated conversations regarding a patient's diabetes management by varying the frequency, content, and tone of messages in light of historical knowledge about the patient and input by the patient's healthcare provider and/or a third party.

In some embodiments, the messaging portal can include an indicator showing the presence of a virtual health coach. For example, the indicator 108 displayed on the messaging portal 102 indicates that the virtual health coach is presently typing a message. The indicator 108 further aids in achieving a conversation that simulates a natural conversation between human users.

As shown in FIG. 1, the virtual health coach's messages may be meant to engage the user in a natural dialog to obtain information necessary to accurately calculate a suitable insulin dosage amount, and can also collect information regarding the user's activities as contextual information that can affect the insulin titration calculation. For example, in FIG. 1, the user's response about having a restless night could impact how a suitable insulin dosage is calculated. More particularly, the patient's blood-glucose levels could be correlated to the patient's restlessness. In other words, the restlessness could be a symptom of the patient's mismanagement of his or her diabetes.

The virtual health coach can create a more natural chat-like engagement by exchanging messages back-and-forth between the user and the chat bot in a natural manner. In some embodiments, the messaging mechanism can also process user-initiated queries regarding the patient's diabetes management. For example, the patient could input questions like "how can I reduce my carb intake," which the virtual health coach can interpret as the patient seeking feedback about managing the user's diet.

In some embodiments, the virtual health coach can launch automatically upon occurrence of certain events. For example, the virtual health coach could launch a simulated conversation every morning at 7 a.m. (e.g., time event) to obtain blood-glucose levels from the user and recommend insulin dosages. In some embodiments, the virtual health coach can run as a background process on the patient's device(s) to engage the patient and collect inputs and contextual information used for insulin titration as needed.

In some embodiments, virtual health coaches implement one or more decision trees with combinations of policies, rules, thresholds, conditions, etc. preset to automatically message users as needed to manage their diabetes. For example, a healthcare provider can personalize a virtual health coach for a particular patient, and the personalized virtual health coach can then operate independently to coach the patient in accordance with the healthcare provider's instructions.

For example, the virtual health coach can be embodied as an algorithm that includes policies comprising a combination of rules, criteria, thresholds, and/or conditions that form a personalized messaging protocol to engage a user in ongoing message exchanges. This can be done mostly or entirely as an automated process that does not require any intervention by a human.

In some embodiments, the virtual health coach is semi-automated in that a healthcare provider or a user other than the patient can influence how the virtual health coach interacts with the patient. For example, a doctor can edit, delete, or add a rule executed by the virtual health coach as needed based on the information collected by the virtual health coach. As such, a patient's doctor can remotely cause the virtual health coach to change its effort to engage the patient at any point in time. Hence, the virtual health coach can be a healthcare provider assisted by the chat bot to communicate with a patient. Moreover, the virtual health coach can include features that allow a user to seek help from a human rather than the virtual health coach by, for example, sending a "help" message.

Thus, the messaging mechanism of the virtual health coach is concerned both with how information is communicated with the user and the content of what is being communicated to improve engagement and the amount of useful information obtained to improve an insulin dosage calculation. The simulated natural communications can be conducted over different types of communications channels including text-based channels, voice-based channels, web-based channels, or combinations thereof. The contextual information including, for example, the user's activities can be used to improve the richness of the data used for the patient's diabetes management.

The data or information collected of the patient can be obtained from a variety of sources, as described in greater detail below. Generally, the user can input data or information in response to prompts from the virtual health coach engaged in a simulated natural conversation. The user inputs can include both information necessary to calculate an insulin dosage and contextual information that could be used to influence the calculation. In some embodiments, a diabetes management platform can use different types of devices to obtain the user inputs or contextual information.

For example, a fitness tracker worn by a patient can collect data of a patient's activity and the virtual health coach can collect the activity data. The collected activity data can be used to improve the insulin titration calculation. For example, in the context of bolus insulin, insulin needs are highly dependent on carbohydrate intake, energy expended, and the patient's metabolism. As such, the patient's activities can be used to adjust an determined carbohydrate intake and/or an determined insulin dosage.

For example, wearing an activity monitor and identifying an hour-long run could affect the estimation of a recommended insulin dosage. In another example, the virtual health coach can obtain contextual information from a device that monitors the patient's interaction with his or her refrigerator at home. The virtual health coach may adjust a diabetes management process based on the patient's activity indicating that the patient was consuming excessive amounts of food on the same day.

In some embodiments, the virtual health coach could make use of data or information obtained from sources that are not necessarily health related. Examples include location dependent services of mobile devices or social media networks. For example, a patient's location can be monitored and track to determine whether the patient ate at a particular restaurant, and the patient's social media postings can be scanned for images of food captured by the patient. As a result, the virtual health coach can analyze various sources of data or information to determine events including what the patient did at a particular location on a given date such as when a patient ate lunch and what the patient ate. This information can be collected by the virtual health coach to adjust an insulin dosage in real-time. Other examples of diverse sources of relevant data or information are described below.

Embodiments of the disclosed technology include techniques for using the aggregate data of numerous patients to improve virtual health coach services. For example, an insulin titration process is typically set by a doctor as part of his or her practice of medicine. However, the data collected of numerous patients can be used by the virtual health coach services to learn ways to improve the way virtual health coaches interact with users and improve the content of messages in simulated natural conversations. Hence, the virtual health coach services can use information gathered of numerous patients to improve the virtual health coaching.

For example, the virtual health coach services can employ A/B testing to identify effective engagement methods. In particular, A/B testing can involve a comparison of two versions of a simulated natural conversation to determine which version performs better to keep users engaged. The virtual health coach services can compare interactions between two slightly different virtual health coaching techniques (i.e., variants A and B) with similarly situated users. The variant that keeps the user engaged longer or obtains higher quality information is declared the winner and could be used with other similarly situated users going forward to improve overall effectiveness by the virtual health coaches.

Figure 2:
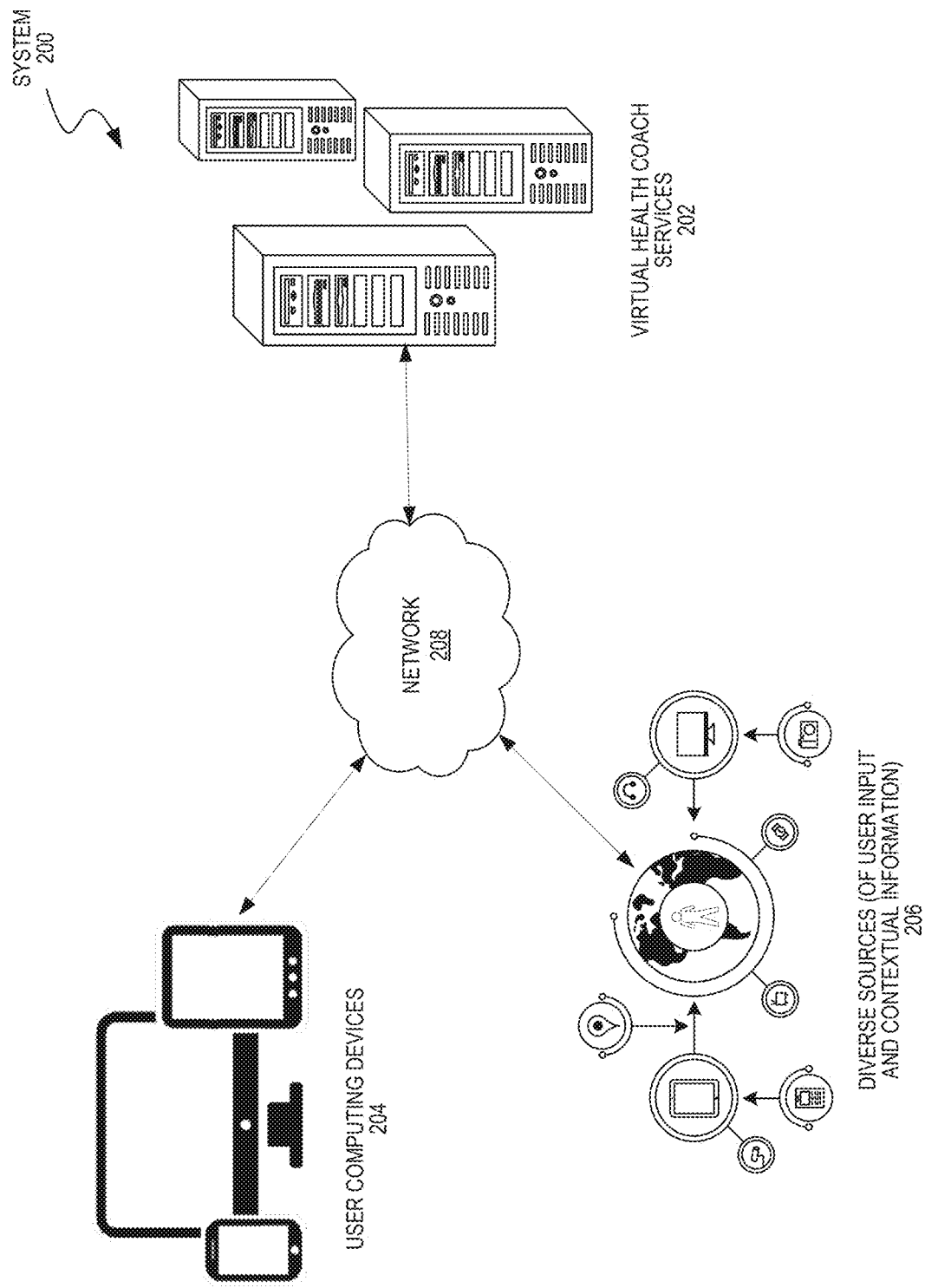
FIG. 2 is a block diagram illustrating a system that implements a virtual health coach platform according to some embodiments of the present disclosure.

FIG. 2 is a block diagram illustrating a system implementing a virtual health coach platform according to some embodiments of the present disclosure. The system 200 is operable to recommend an insulin dosage for a patient by applying inputs and contextual information related to the patient's diabetic condition to an insulin titration algorithm of the platform. The inputs are obtained via a messaging input service of a chat bot that simulates a natural conversation with a human. As a result, the user engaged in the conversation is more likely to interact with the chat bot to provide inputs necessary to determine an insulin dosage. Further, contextual information could be derived from the inputs and applied to the insulin titration algorithm to improve the accuracy of a recommended dosage. Further still, contextual information obtained from sources other than the user device used to engage in the conversation can provide additional useful information for the insulin titration algorithm.

As shown, the system 200 includes components such as virtual health coach services 202 running on one or more servers, user computing devices 204, and other diverse sources 206 for user input and contextual information, all interconnected over a network 208 such as the Internet. The network 208 may include any combination of private, public, wired, or wireless portions. The data or information communicated over the network 208 may be encrypted or unencrypted at various locations or along different portions of the network 208. Each component of the system 200 may include combinations of hardware and/or software to process data or information, perform functions, communicate over the network 208, and the like. For example, any component of the system 200 may include a processor, memory or storage, a network transceiver, a display, OS and application software (e.g., for providing a user interface), and the like. Other components, hardware, and/or software included in the system 200 that would be well known to persons skilled in the art are not shown or discussed herein for the sake of brevity.

The user computing devices 204 (also referred to individually as a user computing device 204) can be used to interact with the system 200. Examples of user computing devices 204 include smartphones (e.g., APPLE IPHONE, SAMSUNG GALAXY, NOKIA LUMINA), tablet computers (e.g., APPLE IPAD, MICROSOFT SURFACE), computers (e.g., APPLE MACBOOK, LENOVO THINKPAD), and any other device that is capable of exchanging data with the virtual health coach services 202 over the network 208.

In some embodiments, a user computing device 204 can automatically determine a geographic location for a query submitted to the self-service server. For example, the user computing device 204 may include a global positioning system (GPS) receiver that receives positioning signals used to determine the geographic location of the user computing device 204. The determined geographic location can be submitted to the virtual health coach services 202 to influence the recommended insulin dosage values for a patient based on the location of the user computing device 204. For example, a calculation for a recommended insulin dosage could be adjusted based on whether the user of the user computing device 204 is the patient visiting the gym or fast food restaurants routinely.

The virtual health coach services 202 may execute on any number of server computers that operate to perform insulin titration processes such as determining an insulin dosage based on inputs and contextual information related to a patient's diabetic condition. The virtual health coach services 202 operate to engage users of the user computing devices 204 in simulated natural conversations to collect data and contextual information from the users and the other diverse sources 206. The collected data and/or information is processed to identify a recommend insulin dosage value for a particular patient.

The virtual health coach services 202 can store insulin titration algorithms that have been personalized for particular patients. For example, a personalized insulin titration algorithm may include a combination of rules for determining a basal insulin dosage. A set of rules of an insulin titration algorithm for a particular patient may be personalized by the patient's doctor in accordance with the doctor's medical practice.

In some embodiments, an insulin titration algorithm may include policies having rules, criteria, conditions, and/or thresholds that are set by a doctor to apply the policies in a manner that is personalized for a patient. For example, an insulin titration algorithm may include a rule set for a patient of a particular gender, age, and having a diagnosed diabetic condition. An insulin titration algorithm for another patient may include a different set of rules based on that patient's particular circumstances. In some embodiments, an insulin titration algorithm may include the same set of rules that are applied in different ways to different patients in accordance with the instructions of healthcare providers to achieve the same or different objectives. Moreover, the insulin titration algorithms can be adjusted as needed in response to any changed circumstances. For example, a patient's doctor may adjust the patient's personalized insulin titration algorithm based on the patient's progress or lack thereof.

In some embodiments, the virtual health coach services 202 can establish a direct connection between a user computing device 204 and devices of the other diverse sources 206 based on the activity of a user of the user computing device 204. For example, a user engaged in a natural conversation with a chat bot my signal a need for help whereby the virtual health coach services 202 can establish a link between the user of the user computing device 204 and a healthcare professional of the other diverse sources 206. Further, the user of the user computing device 204 engaged in a chat with the virtual health coach services 202 can request a direct connection to the provider over a variety of channels such as a web channel or voice channel.

In some embodiments, the data input by the user of the user computing device 204 engaged in a simulated conversation with a chat bot about a diabetic patient and/or contextual information may be communicated automatically to the patient's healthcare provider upon establishing a direct connection so that the healthcare provider can seamlessly continue the conversation with the user. Accordingly, data or information from healthcare providers, other devices, or services can be provided by the diverse sources 206 over the network 208 directly to the user computing devices 204 or indirectly through the virtual health coach services 202.

The other diverse sources 206 may include any number of servers or other computing resources that can collect, store, and/or provide data or information to the virtual health coach services 202 over the network 208 for use in determining insulin dosages for particular patients. The diverse sources 206 may include any source of healthcare-related information. For example, the diverse sources 206 may include any providers such as medical facilities, private offices, or devices administered by healthcare professionals. In some embodiments, the data or information may include at least portions of medical records utilized in insulin titration algorithms.

For example, medical records information may include the instructions from a patient's doctor that are used to personalize an insulin titration algorithm for the patient. The diverse sources 206 may also include data or contextual information related to or affecting the diabetic condition of a patient obtained from a variety of devices, which could be used to improve insulin dosage estimations. Examples of diverse sources are described in reference to FIG. 4.

The virtual health coach services 202 may administer the messaging mechanism capable of engaging a user of the user computing device 204 in a natural conversation with a chat bot. In some embodiments, the messaging mechanism could be part of a portal that allows users to exchange information related to a patient's diabetic condition.

Examples of the portal include a website, mobile app, or any communications mechanism allowing for bidirectional natural conversational communications between humans, where the conversation is engaged via that mechanism by a user of the user computing device 204 and a chat bot implemented as a virtual health coach. For example, a user of the user computing device 204 can have a simulated natural conversation with a chat bot to provide information used by a patient's insulin titration algorithm to determine a recommended insulin dosage based user inputs and/or contextual information applied to rules personalized by the patient's healthcare provider.

Figure 3:
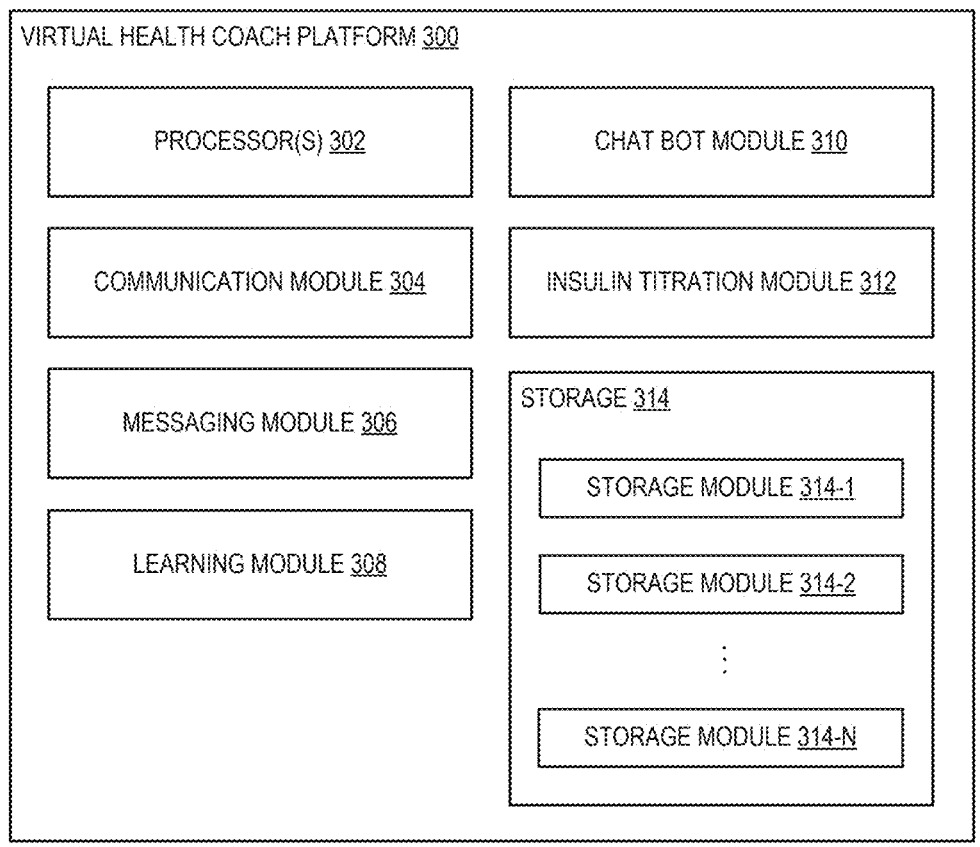
FIG. 3 is a block diagram illustrating a virtual health coach platform according to some embodiments of the present disclosure.

FIG. 3 is a block diagram illustrating a virtual health coach platform according to some embodiments of the present disclosure. The virtual health coach platform 300 ("platform 300") can include components or modules that collectively operate to engage patients in a personalized diabetes management program that involves insulin titration. As used herein, a "component" or "module" may refer to a part or independent unit of hardware and/or software that performs one or more distinct functions. In some instances, a module is self-contained, separable, and/or interchangeable relative to other modules.

As shown, the platform 300 includes one or more processors 302, a communication module 304, a messaging module 306, a learning module 308, a chat bot module 310, an insulin titration module 312, and storage 314. Other embodiments of the platform 300 may include some or all of these modules or components, along with other modules and/or components that could be derived based on this disclosure or known to persons skilled in the art but not shown herein for the sake of brevity.

The processor(s) 302 can execute modules from instructions stored in storage modules 314, which can be any device or mechanism capable of storing information. The communication module 304 may manage communication between components of the platform 300 and/or between the platform 300 and another computing device. For example, the communication module 304 facilitates communication of user inputs or contextual information related to a patient's diabetes management program. The received inputs or information may be wirelessly uploaded by the user's computing device (e.g., user computing device 204) or other device (e.g., diverse sources 206) over a network (e.g., network 208) to a server computer (e.g., servers of virtual health coach services 202).

The communication module 304 facilitates the exchange of communications between a user computing device and the chat bot module 310 in a simulated natural conversation. Further, communication module 304 may transmit notifications of insulin dosages to a computing device associated with a patient or the patient's healthcare provider. The user inputs or contextual information communicated by the communication module 304 can be stored in storage 314, one or more particular storage modules (e.g., storage modules 314-1 through 314-n), a remote storage accessible to the platform 300, or some combination thereof.

The messaging module 306 can generate a messaging interface that allows a user (e.g., a diabetic patient) to interact with the platform 300. In some embodiments, the messaging interface may be presented via a web browser, desktop software program, mobile app, or over-the-top (OTT) application. Accordingly, the messaging interface may be accessible via a mobile phone, tablet computer, personal computer, game console (e.g., SONY PLAYSTATION or MICROSOFT XBOX), wearable electronic device (e.g., a watch or fitness tracker), network-connected "smart" devices, virtual/augmented reality systems (e.g., OCULUS RIFT or MICROSOFT HOLOLENS), etc.

The chat bot module 310 can parse inputs received by a user computing device from a user engaged in a simulated conversation about a diabetic patient in order to extract data or information that is useful for the insulin titration module 312 to recommend insulin dosages for the patient. More specifically, the chat bot module 310 implements a chat bot as a virtual health coach or other automated communications services to communicate with a patient via a mobile/web-based portal in a simulated natural conversation. In other words, a chat bot is implemented as a virtual health coach by the chat bot module 310 to engage a user (e.g., patient) of a client device in a simulated natural conversation.

For example, a virtual health coach could be part of a cloud service including the chat bot module 310, which communicates routinely with a user via a local portal (e.g., mobile app) resident on the user's smartphone or via a network portal (e.g., website) linked to the cloud. In some embodiments, the chat bot module 310 can be part of a self-contained service that resides on a client device. As such, the user input or contextual information collected for a patient can be partly or entirely processed locally without the need to communicate any part of the simulated natural conversation over a network.

In some embodiments the chat bot module 310 is launched based on a schedule set by a patient's healthcare provider or is launched based on events identified from the patient's activity. In some embodiments, the chat bot module 310 can monitor user inputs and respond dynamically as needed to effectively engage a user. In some embodiments, the chat bot module 310 can response to data obtained from devices other than the user computing device by initiating a simulated natural conversation with the user of the client device.

For example, the chat bot module 310 may receive an indication that the patient is located at a restaurant based on the location determined by the patient's smartphone or information posted by the patient on his or her social network webpage. In response, the chat bot module 310 can cause the virtual health coach services to initiate a conversation with the patient about the user's intake, which can be used to adjust a recommended insulin dosage. Those skilled in the art will recognize that such recommended insulin dosages represent proposed dosages that may need to be confirmed by a medical professional.

The insulin titration module 312 can process the parsed input data or contextual information to determine a recommended insulin dosage for a particular patient. Generally, the extracted values will include a patient's blood-glucose levels as input by a user of a computing device engaged in a simulated natural conversation with a chat bot. The extracted values are processed in accordance with an algorithm that has been personalized for the particular patient based on instructions from the patient's healthcare provider.

In some embodiments, the insulin titration module 312 can process contextual information derived from a simulated natural conversation or obtained from devices other than the client device executing the simulated natural conversation. For example, a fitness tracker worn by the patient can perform machine-to-machine communications to send the patient's fitness information for the insulin titration module 312 automatically (e.g., without user intervention).

In some embodiments, the user input, contextual information, and/or values extracted therefrom can be stored in the storage modules 314 along with the values calculated by the insulin titration module 312 based on the extracted values. In this way, the insulin titration module 312 can use the stored historical data to improve the recommended insulin dosages or track the users progress or lack of progress. In some instances, the stored data or information could be shared with other authorized users or processed with similar data or information from the other users to improve the operations of the virtual health coach platform 300 based on the data or information of numerous users. Accordingly, the insulin titration module 312 may parse data or information and analyze extracted values of numerous users over a period of time in order to track the effectiveness of a diabetes management program.

In some embodiments, the learning module 308 can utilize the user inputs and/or contextual information to improve the virtual health coach platform 300. For example, the learning module 308 can aggregate collected user inputs and contextual information from numerous users associated with numerous patients, and process that collected inputs or information to obtain insights the effectiveness of certain modes of simulated natural conversation processes, track patients, and formulate new modes of simulated natural conversations or new insulin titration algorithms. In some embodiments, the learning module 308 can discover new techniques for improving the effectiveness of engaging with users and improve the accuracy of existing insulin titration algorithms.

For example, the learning module 308 may discover that patients with certain attributes are more responsive to certain conversation techniques compared to other types of patients. This learned data can be used to further personalize the way that the chat bot module 310 engages users. The learning module 308 can employ various machine learning algorithms and techniques to improve the effectiveness of the chat bot module 310 and/or insulin titration module 312. Examples of machine learning algorithms/techniques include Naïve Bayes Classifier algorithms, K Means Clustering algorithms, Support Vector Machine algorithms, linear regression, logic regression, and artificial neural networks.

In one example, the learning module 308 can implement an form of A/B testing to refine the conversation techniques implemented by the chat bot module 310. A/B testing (also known as split testing or bucket testing) is a method of comparing two versions of a webpage, app, or a technique against each other to determine which one performs better. A/B testing is essentially an experiment where two or more variants of a technique are presented to users at random or pseudo-randomly, and statistical analysis is used to determine which variation performs better for a given objective.

Performing an A/B test that directly compares a variation against a current experience allows for asking focused questions about changes to a technique, and then collect data about the impact of that change. Testing takes the guesswork out of the optimization of simulated natural conversations and enables data-informed decisions that shifts conversations from speculating about what works to having evidence about what is most effective. By measuring the impact that changes have on certain metrics, the learning module 308 can ensure that every change produces improved results.

For example, in A/B testing of a simulated conversation technique, certain content of a conversation, mode of conversation, or subject of conversation is varied between two populations of users. The change can be as simple as setting a humorous tone in one simulated mode of conversation and setting a serious tone in another simulated mode of conversation. A first group of users could be subjected to the first mode and a second group of users could be subjected to the second mode. The metrics used to determine which mode is superior could include the amount of useful data that was extracted from users, the responsiveness of users, and their level of engagement in the conversations (e.g., the period of time users remained engaged or whether they answered most questions or asked follow-up questions).

In another example, a virtual health coach can run A/B testing and/or other dosage experimentation that helps with the insulin titration process. For example, the virtual health coach can begin the titration process by asking the patient to fast or refrain from glucose for a day or two, and then begin suggesting different dosage the following days. Two variants of the same questions can be presented to different groups of users to identify the most effective titration process.

Figure 4:
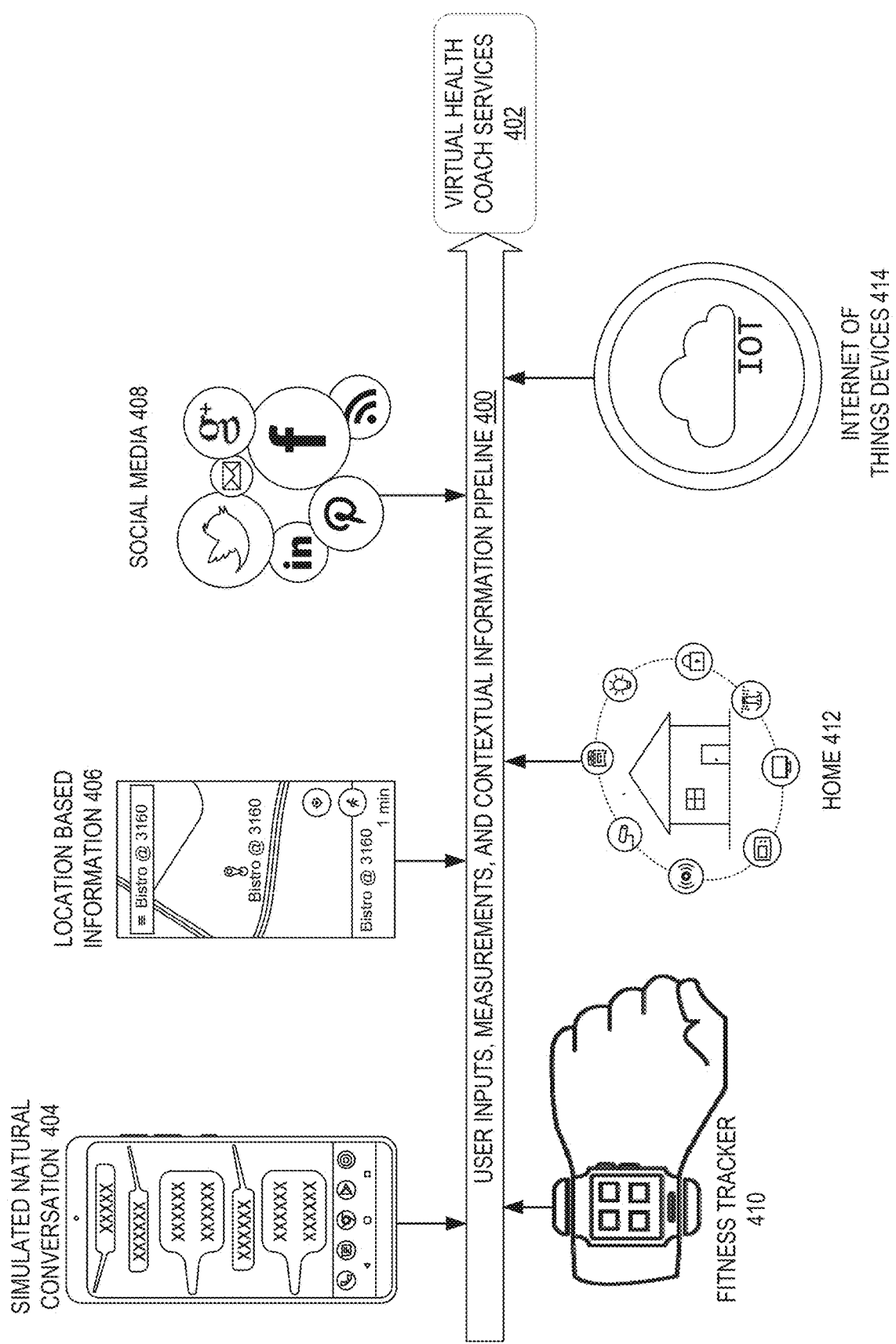
FIG. 4 is a block diagram illustrating a pipeline for user inputs and contextual information used to personalize a virtual health coach according to some embodiments of the present disclosure.

The virtual health coach platform 300 can also collect contextual information (e.g., real-time health/activity state from mobile/wearable sensors, self-reported health/activity state, environmental state from mobile/wearable sensors, etc.) to help or improve with the insulin titration algorithm. For example, FIG. 4 is a block diagram illustrating a pipeline of user inputs and contextual information for performing personalized insulin titration processes according to some embodiments of the present disclosure. The pipeline 400 sources user inputs and/or contextual information from various diverse sources for the virtual health coach services (e.g., virtual health coach services 202). The pipeline 400 represents one or more communications channels (e.g., network 208) and devices (e.g., user computing devices 204 or diverse sources 206) operating as sources of data used to build the patient's profile.

Examples of the diverse sources (e.g., diverse sources 206) illustrated in FIG. 4 include a simulated conversation 404, information related to a patient's location 406, social media 408, the patient's fitness tracker 410, devices at the patient's home 412 monitoring the patient's activities, and virtually any other computing devices such as IoT devices 414 that can communicate user inputs and/or contextual information useful for the virtual health coach services 402.

For example, the simulated conversation 404 can be engaged between the user of a smartphone and a chat bot to collect user inputs necessary for the titration process. In addition to the user inputs provided by the user of the computing device to the chat bot, contextual information can be derived from simulated conversations. For example, the context may include exchanges between the user and a chart bot that constitute "small talk" in ordinary situations but could provide insights into the user's activity that could impact their ability to self-manage their diabetes.

For example, a user's level of engagement that falls below a certain threshold can indicate that the user is losing interest in managing his or her diabetes. In another example, communications about the patient's activities posed in the context of a simulated conversation about the titration process could include contextual information used to adjust the titration process. For example, an indication that a patient consumed a significant amount of food or was engaged in substantial cardiovascular activity can be used to adjust a recommend bolus insulin dosage.

Examples of the location information 406 include a patient's location, which could be determine by the GPS receiver of the patient's smartphone. The location information 406 can be used to determine, for example, whether the patient visited a restaurant or a gym. If so, the chat bot can engage the patient with a simulated conversation to obtain more details about what the user ate at the restaurant or the exercise that the patient participated in while at the gym. This contextual information can be used to adjust the insulin titration process or track the success or lack thereof by a patient to manage his or her diabetes.

Examples of information from social media 408 include posts related to a patient and made available on social media. For example, a patient may take a picture of his or her dinner and post it on FACEBOOK. The image or related content may be sent over the pipeline 400 to the virtual health coach services 402. The image can be analyzed by the virtual health coach services 402 to determine whether a virtual health coach should initiate a simulated conversation with the patient to inquire about the patient's consumption habits. On the other hand, the virtual health coach services 402 may account for the meal by adjusting the insulin titration process without ever engaging the patient in the simulated conversation.

Examples of contextual information from the fitness tracker 410 could include data or information about the user's activities such as whether the user is exercising, the duration and rigor of the exercise, and related physiological indicators of the user such as heart rate. This fitness information can be used alone or in combination with other contextual information to influence the simulated conversation or titration processes of the virtual health coach services 402. For example, the fitness information can be used in combination with the location information 406 to learn about the user's exercise habits including whether the user undergoes a more rigorous exercise at a gym rather than at home. This information can be used by the virtual health coach services 402 to improve the future simulated conversation. For example, the virtual health coach services 402 can ask the patient questions in the context of his or her experience at a particular gym.

Examples of contextual information obtained by monitoring the patient's home 412 can include intelligent appliances that monitor the user's activities. For example, a smart refrigerator can detect the frequency that a patient opens the refrigerator and alert the virtual health coach services 402 to engage in a simulated conversation in response to this activity. In another example, the home 412 can include a virtual assistant such as the AMAZON ECHO, which uses natural language processing to match user text and voice inputs to execute commands. In some embodiments, the virtual health coach services 402 can engage the patient in a simulated conversation via a virtual assistant as part of usual daily interactions with the virtual assistant.

Examples of internet of things (IoT) devices 414 include any devices that include components to capture contextual information (e.g., environmental sensors) and that can connect over a network to the virtual health coach services 402. For example, vehicles or a network of cameras can capture information about a patient's activities and forward that information to the virtual health coach services 402 to improve or adjust simulated conversations or titration processes. The examples shown in FIG. 4 are not meant to be limiting. Rather, the virtual health coach services 402 can collect user inputs or contextual information from any device capable of generating or capturing the user inputs or contextual information and communicating it to the virtual health coach services 402.

In some embodiments, user inputs or contextual information can be collected by the pipeline 400 periodically (e.g., hourly, daily) or on demand. For example, the virtual health coach services 402 can administer a messaging portal that engages a patient in simulated conversations periodically to receive inputs. The user inputs or contextual information may indicate an ongoing severity of symptoms experienced by the patient. In some embodiments, these user inputs and contextual information can be used to update the patient's profile.

In some embodiments, the user inputs or contextual information can be used for compliance monitoring. For example, a mobile app may prompt the user to input whether the patient is complying with a desired behavior, such as regularly exercising. Tracking a patient's compliance in combination with data about the patient's outcomes can be used to determine whether the prescribed diabetes management program is effective at managing the patient's diabetes.

In some embodiments, the user inputs or contextual information can be used to alert healthcare professionals of the patient's failure to comply. For example, upon receiving an input at the user computing device about a patient's noncompliance or after a designated period of time has elapsed without receiving confirmation of the patient's compliance, the virtual health coach services 402 may issue a notification to a healthcare provider's device about the patient's noncompliance. The notice can be used to alert the healthcare provider to take action when compliance is critical.

The types of user inputs or contextual information and their sources are not limited to the examples described above. Instead, these examples are illustrative of the diverse types of data and sources that can be employed to collect data into the pipeline 400 to perform an insulin titration process. Unlike conventional systems that collect limited information about a patient, the disclosed technology makes use of diverse data types from diverse sources to identify how to treat a patient based on his or her particular situation or circumstances.

Figure 5:
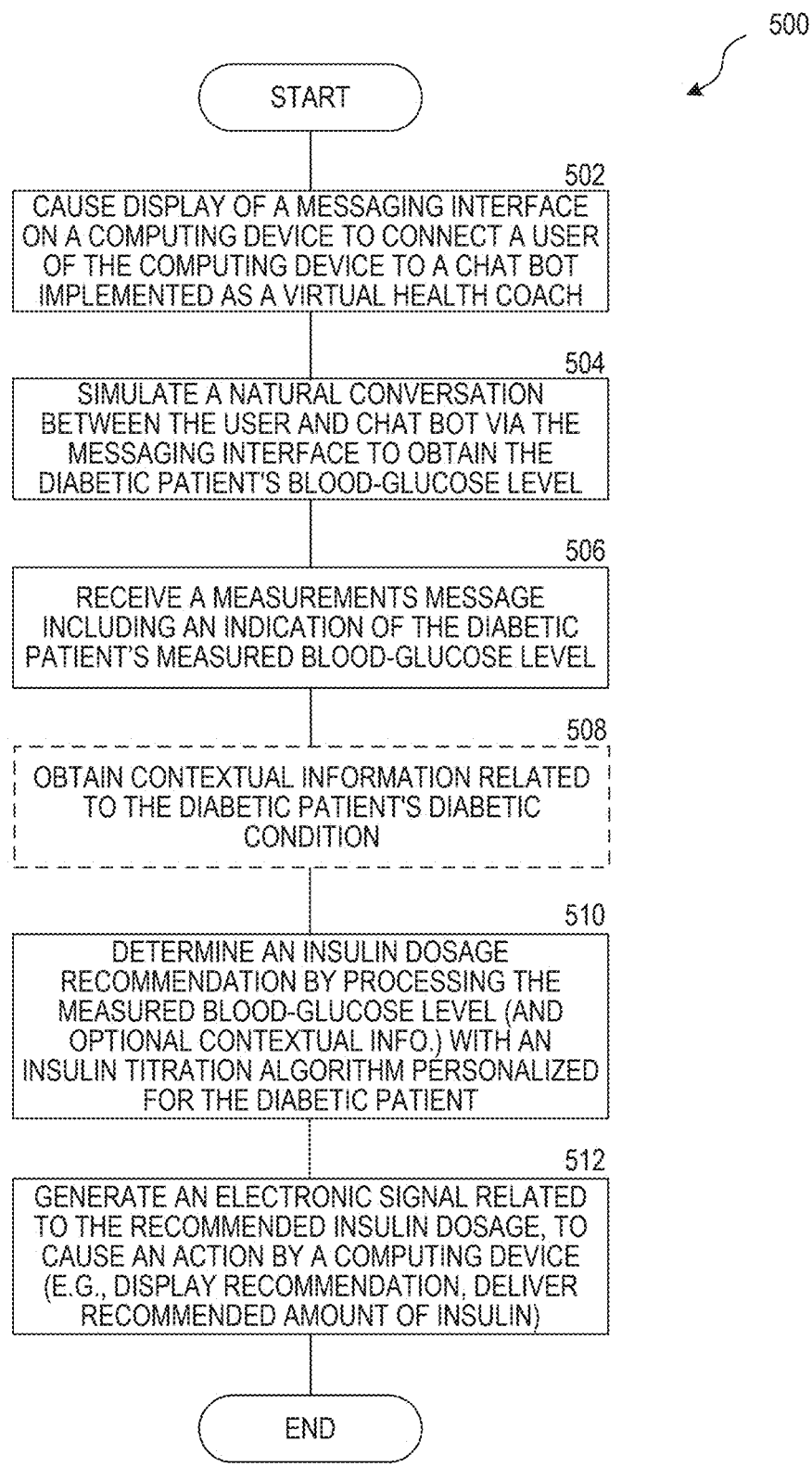
FIG. 5 is a flowchart illustrating a process of a virtual health coach platform to obtain user inputs and contextual information for aiding a user in diabetes self-management according to some embodiments of the present disclosure.

FIG. 5 is a flowchart illustrating a process of a virtual health coach platform to determine a recommended insulin dosage for a patient according to some embodiments of the present disclosure. In particular, the computer-implemented process 500 can improve the efficacy of diabetes self-management with automated personalized computer engagement that reliably obtains user inputs and/or contextual information used to determine a suitable insulin dosage of an insulin titration process to treat the diabetic patient. The process 500 can be performed by any combination of one or more devices of a virtual health coach platform including a user computing device, server computer(s) of virtual health coach services, or any other computing device.

In step 502, a messaging interface is caused to display on a display of a computing device. The messaging interface communicatively couples the user (e.g., patient) of the computing device to a computer program operable to simulate a conversation with human users. In some embodiments, the computer program is a chat bot implemented as a virtual health coach.

In step 504, a natural conversation is simulated between the user of the computing device and the chat bot. The simulated natural conversation can include a message generated by the chat bot and presented via the messaging interface to obtain a measurement of the diabetic patient's blood-glucose level.

In some embodiments, the simulated natural conversation may include textual messages or voice-based messages exchanged between the user and the computer program.

In step 506, a user-input message responsive to the message generated by the computer program is received, where the user-input message includes an indication of the diabetic patient's measured blood-glucose level.

In step 508, the process 500 may optionally obtain contextual information related to the diabetic patient's diabetic condition. For example, the contextual information can be derived the contextual information from content included in the simulated natural conversation between the user of the computing device and the computer program via the messaging interface. In particular, the simulated natural conversation can include messages exchanged between the user and the chat bot, and those messages can be parsed to identify a physical activity by the diabetic patient. In some embodiments, the simulated natural conversation has a frequency, content, and tone that is personalized for a diabetic patient to improve efficacy of insulin titration self-management by the diabetic patient.

In some embodiments, the contextual information is obtained over a computer network from a computing device other than the computing device being used by the user. The contextual information may indicate a physical activity of the diabetic patient. Examples of the other computing device includes an activity tracker worn by the diabetic patient, a monitoring device (e.g., camera) that monitors physical activities of the diabetic patient, or any IoT device. Other sources of contextual information can include information indicative of a physical location of the diabetic patient, or information related to the diabetic patient and obtained from a social media network.

Figure 6:
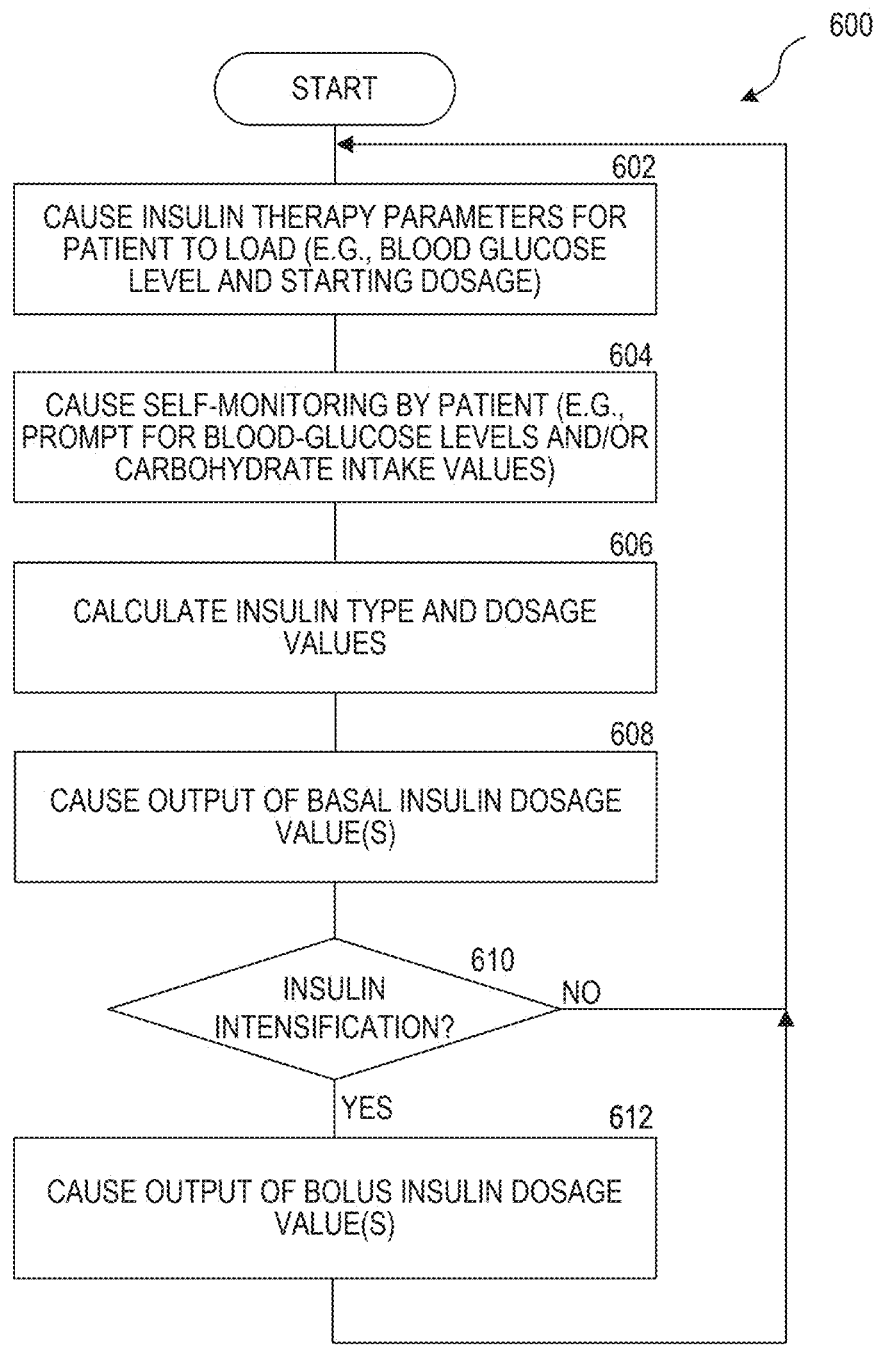
FIG. 6 is a flowchart illustrating an example of a personalized insulin titration algorithm according to some embodiments of the present disclosure.

In step 510, a recommended insulin dosage is determined to treat the diabetic patient by processing the patient's measured blood-glucose level obtained via the messaging interface with an insulin titration algorithm that is personalized for the diabetic patient. In some embodiments, the insulin titration algorithm includes a set of rules personalized for the diabetic patient by a healthcare provider to treat the diabetic patient. An example of an insulin titration algorithm is illustrated in FIG. 6 described below.

In some embodiments, the recommended insulin dosage is determined in accordance with an insulin titration algorithm as a function of the contextual information in addition to the diabetic patient's measured blood-glucose level included in the user input message. For example, the recommended insulin dosage may be adjusted based on the contextual information.

In step 512, an electronic signal including an indication of the recommended insulin dosage is generated. The electronic signal can be configured to cause a corresponding action to be performed by a computing device. For example, the corresponding action could be to display, via the messaging interface on the display of a computing device, a message including the recommended insulin dosage. In another example, the corresponding action is to cause an insulin delivery device to deliver an amount of insulin corresponding to the recommended insulin dosage. In some embodiments, the recommended insulin dosage is a basal insulin dosage or a bolus insulin dosage.

The process 500 can be implemented across a network of distributed users of user devices of respective computing devices communicatively coupled to respective chat bots, which are each operable to simulate a natural conversation with human users. For example, one or more servers running virtual health coach services can simulate many natural conversations between the users of respective computing devices and the chat bots, where each simulated natural conversation is customized for a human patient based on a respective set of rules personalized by the patient's healthcare provider.

The server computer can receive and exchange messages between each user-chat bot combination engaged in a simulated natural conversation. Those messages may include content indicative of a patient's blood-glucose level, contextual information indicative of the patient's physical activity, and a recommended insulin dosage determined by the one or more processors based on the patient's blood-glucose level and contextual information.

In some embodiments, the virtual health coach services can perform A/B testing by generating two variants of a simulated natural conversation engaged in by two similarly situated groups of the plurality of users. The virtual health coach services can correlate each of the two variants with a degree of engagement of a user of a computing device engaged in a simulated natural conversation such that one variant has a greater degree of engagement compared to the other variant. Then, the variant with the greater degree of engagement is designated as a preferred variant for subsequent simulated natural conversations between a user of a computing device and a chat bot.

As indicated above, an insulin titration algorithm of the virtual health coach service may be personalized for a patient. A patient that starts insulin therapy is typically counseled about the recognition, prevention, and treatment of hypoglycemia. An insulin titration algorithm is then personalized for the patient. An example of such a personalized algorithm is illustrated in FIG. 6, which shows a combination of steps to output at least one of basal insulin or bolus insulin values. The virtual health coach service can aid a patient with insulin therapy by coaching the patient in accordance with a patient's personalized algorithm. The personalized algorithm may cause a user device to prompt for certain inputs used to determine an insulin type (e.g., basal, bolus) and insulin values (e.g., amount, timing) to coach the patient to comply with a particular insulin therapy, particularly if glycemic target levels are not being achieved by the patient.

In step 602, the personalized algorithm can cause the patient's insulin therapy parameters to load for use by the virtual health coach service. These values may include, for example, a target fasting blood-glucose level of 4.0 to 7.0 mmol/L, a starting dose of 10 units administered once daily (e.g., at bedtime), and a titration of 1 unit per day until target levels are achieved. The insulin can then be titrated to achieve target levels as a function of the loaded values and patient-dependent factors. For example, in elderly or normal weight patients, a personalized algorithm may implement a relatively lower starting dose, slower titration, and/or higher targets.

In step 604, the personalized algorithm can cause the virtual health coach service to prompt a user for self-monitoring inputs. For example, an insulin titration algorithm could have rules to determine when and how to prompt the patient for a fasting blood-glucose measurement at least once daily in order to safely titrate insulin. In some embodiments, the insulin titration algorithm could have rules to determine when and how to prompt the patient for information regarding food intake. For example, bolus insulin therapy requires monitoring carbohydrate intake, which is preferably kept constant.

In step 606, an insulin type and one or more dosage values are calculated as a function of the patient's inputs and other patient-dependent factors. The dosage values may include an amount and timing to recommend administering insulin. For example, in basal insulin therapy, an insulin dose should not be increased if the patient experiences two episodes of hypoglycemia (blood-glucose <4.0 mmol/L) in 1 week or any episode of nocturnal hypoglycemia. In another example, for fasting blood-glucose levels consistently below 5.5 mmol/L, a reduction of 1-2 units of insulin may be determined to avoid nocturnal hypoglycemia. In yet another example, the personalized algorithm may determine that oral antihyperglycemic agents need to be reduced when daytime hypoglycemia occurs.

In step 608, the personalized algorithm can cause the virtual health coach service to output the calculated basal insulin values to aid the patient in self-insulin titration.

In some embodiments, the basal insulin is augmented with bolus insulin. For example, in step 610, it is determined whether intensification of insulin therapy is necessary and, if so, the personalized algorithm can recommend an injection of mealtime insulin for a main meal or breakfast. Otherwise, the personalized algorithm loops to continue basal insulin therapy.

In step 612, the personalized algorithm can cause the virtual health coach service to output a bolus insulin when intensification of insulin therapy is necessary. For example, a bolus insulin can be administered once daily to improve basal insulin therapy. The patient's healthcare provider can personalize the bolus insulin therapy in addition to, or instead of, the basal insulin therapy.

The personalized algorithm can cause the virtual health coach service to load bolus insulin related values in step 602. Examples of the values include a starting dose of 2 to 4 units that can be titrated by 1 unit daily to achieve target values. For example, the targets can include two-hour post-meal glucose of 10.0 mmol/L (or s 8.0 mmol/L in certain cases) or pre-meal glucose of the next meal of 4.0 to 7.0 mmol/L. Also, oral antihyperglycemic agents may need to be reduced or stopped particularly if daytime hypoglycemia occurs.

Thus, the personalized algorithm can cause the virtual health coach service to output the calculated basal and/or bolus insulin in a manner that aids the patient in self-insulin titration. The insulin therapy can cycle as needed in accordance with the personalized algorithm to achieve targets.

Another example of an insulin therapy that can be implemented with a personalized algorithm includes basal-bolus insulin titration. For example, a total daily dose of 0.3 to 0.5 units/kg can be set for the patient in step 602. Then, in step 606, a calculated daily dose can be allotted as 40% of the total insulin as basal insulin and 20% of the total insulin as bolus insulin three-times per day using either rapid-acting insulin analogue or short-acting insulin.

Figure 7:
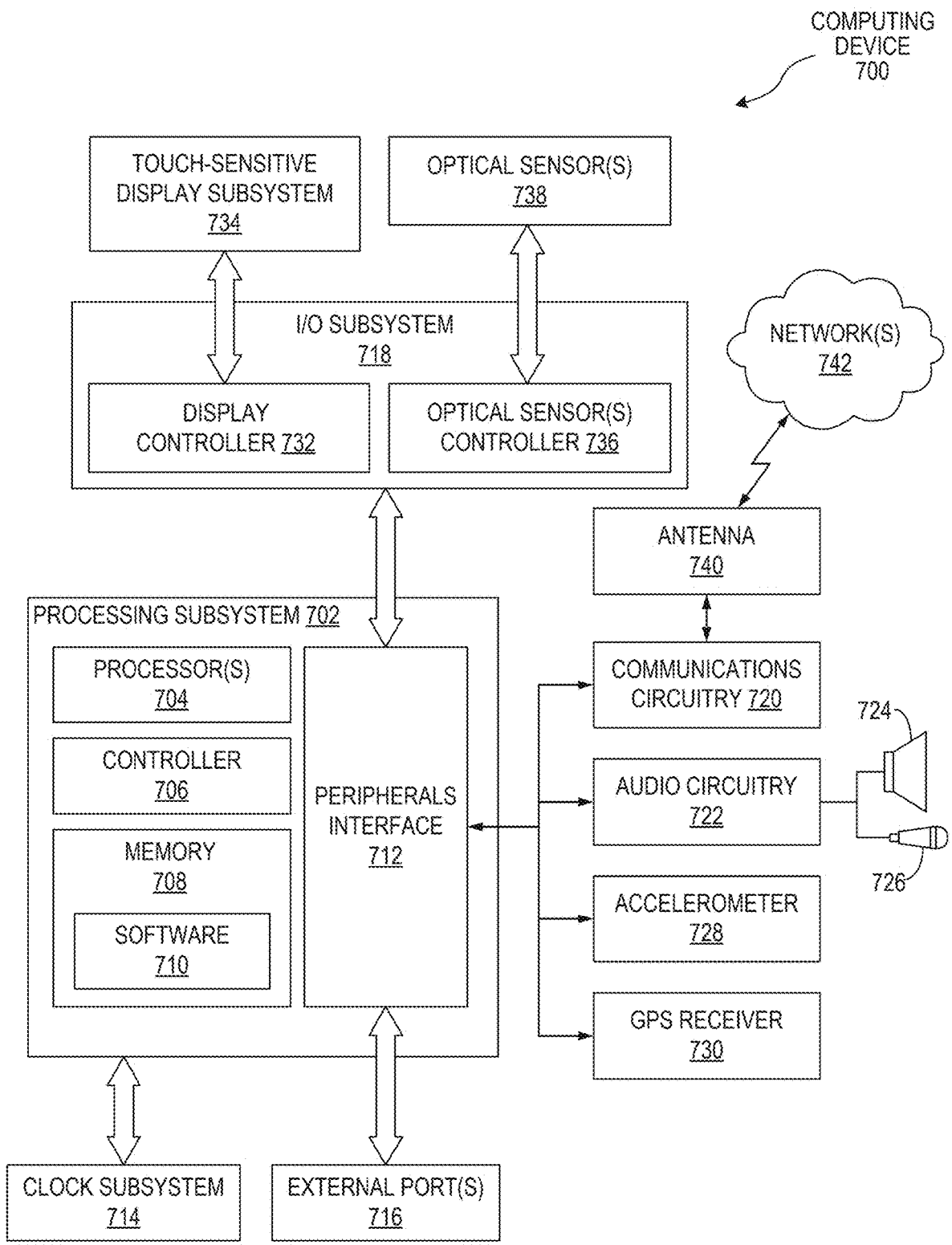
FIG. 7 is a block diagram illustrating an example computing device in which aspects of the disclosed technology can be embodied.

FIG. 7 is a block diagram illustrating an example computing device (e.g., computing device 100) in which aspects of the disclosed technology can be embodied. For example, the virtual health coach platform (e.g., virtual health coach platform 300 of FIG. 3) may be hosted on the computing device 700. The computing device 700 may include generic components and/or components specifically designed to carry out the disclosed technology. The computing device 700 may be a standalone device or part of a distributed system (e.g., system 200 of FIG. 2) that spans networks, locations, machines, or combinations thereof. For example, components of the computing device 700 may be included in or coupled to a system-on-chip (SOC), a single-board computer (SBC) system, a desktop or laptop computer, a kiosk, a mainframe, a mesh of computer systems, or combinations thereof.

In some embodiments, the computing device 700 can operate as a server device or a client device in a client-server network environment, or as a peer machine in a peer-to-peer system. In some embodiments, the computing device 700 may perform one or more steps of the disclosed embodiments in real-time, near real-time, offline, by batch processing, or combinations thereof.

The computing device 700 includes a processing subsystem 702 that includes one or more processors 704 (e.g., central processing units (CPUs), application specific integrated circuits (ASICs), and/or field programmable gate arrays (FPGAs)), a memory controller 706, memory 708 that can store software 710, and a peripherals interface 712. The memory 708 may include volatile memory (e.g., random-access memory (RAM)) and/or non-volatile memory (e.g., read-only memory (ROM)). The memory 708 can be local, remote, or distributed. The computing device 700 can also include a clock subsystem 714 that controls a timer for use in some embodiments. The components of the computing device 700 are interconnected over a bus (not shown) operable to transfer data between hardware components.

The peripherals interface 712 is coupled to one or more external ports 716 which can connect to an external power source, for example. The peripherals interface 712 is also coupled to an I/O subsystem 718. Other components coupled to the peripherals interface 712 include communications circuitry 720, audio circuitry 722 for a speaker 724 and a microphone 726, an accelerometer 728, a GPS receiver 730 (or global navigation satellite system (GLONASS) or other global navigation system receiver), and other sensors (not shown). The GPS receiver 730 is operable to receive signals concerning the geographic location of the computing device 700. The accelerometer 728 can be operable to obtain information concerning the orientation (e.g., portrait or landscape) of the computing device 700.

The I/O subsystem 718 includes a display controller 732 operative to control a touch-sensitive display system 734, which further includes the touch-sensitive display of the computing device 700. The I/O subsystem 718 also includes an optical sensor(s) controller 736 for one or more optical sensors 738 of the computing device 700. The I/O subsystem 718 includes other components (not shown) to control physical buttons.

The communications circuitry 720 can configure the antenna 740 of the computing device 700. In some embodiments, the antenna 740 is structurally integrated with the computing device 700 (e.g., embedded in the housing or display screen) or coupled to the computing device 12 through the external ports 716. The communications circuitry 720 can convert electrical signals to/from electromagnetic signals that are communicated by the antenna 740 to networks 742 (e.g., network 208 of FIG. 2) or other devices. For example, the communications circuitry 720 can include radio frequency (RF) circuitry that processes RF signals communicated by the antenna 740.

The communications circuitry 720 can include circuitry for performing well-known functions such as an RF transceiver, one or more amplifiers, a tuner, oscillators, a digital signal processor, a CODEC chipset, a subscriber identity module (SIM card or eSIM), and so forth. The communications circuitry 720 may communicate wirelessly via the antenna 740 with the networks 742 (e.g., the Internet, an intranet and/or a wireless network, such as a cellular network, a wireless local area network (LAN) and/or a metropolitan area network (MAN)) or other devices.

The software 710 can include an OS software program, application software programs, and/or modules (e.g., communication module 304, messaging module 306, learning module 308, chat bot module 310, insulin titration module 312, storage modules 314 of FIG. 3). For example, a GPS module can determine the location of the computing device 700 based on the GPS signals received by the GPS receiver 730. The GPS module can provide this information to components of the computing device 700 for use in various applications (e.g., to provide location-based contextual information).

A software program, when referred to as "implemented in a computer-readable storage medium," includes computer-readable instructions stored in the memory (e.g., memory 708). A processor (e.g., processor 704) is "configured to execute a software program" when at least one value associated with the software program is stored in a register that is readable by the processor. In some embodiments, routines executed to implement the disclosed embodiments may be implemented as part of OS software (e.g., Microsoft Windows and Linux) or a specific software application, component, program, object, module, or sequence of instructions referred to as "computer programs."

Computer programs typically comprise one or more instructions set at various times in various memory devices of the computing device 700, which, when read and executed by the processor 704, will cause the computing device 700 to execute functions involving the disclosed embodiments. In some embodiments, a carrier containing the aforementioned computer program product is provided. The carrier is one of an electronic signal, an optical signal, a radio signal, or a non-transitory computer-readable storage medium (e.g., the memory 708).

Operation of the memory 708, such as a change in state from a binary one (1) to a binary zero (0) (or vice versa) may comprise a visually perceptible physical change or transformation. The transformation may comprise a physical transformation of an article to a different state or thing. For example, a change in state may involve accumulation and storage of charge or a release of stored charge. Likewise, a change of state may comprise a physical change or transformation in magnetic orientation or a physical change or transformation in molecular structure, such as a change from crystalline to amorphous or vice versa.

Aspects of the disclosed embodiments may be described in terms of algorithms and symbolic representations of operations on data bits stored in memory. These algorithmic descriptions and symbolic representations generally include a sequence of operations leading to a desired result. The operations require physical manipulations of physical quantities. Usually, though not necessarily, these quantities take the form of electric or magnetic signals that are capable of being stored, transferred, combined, compared, and otherwise manipulated. Customarily, and for convenience, these signals are referred to as bits, values, elements, symbols, characters, terms, numbers, or the like. These and similar terms are associated with physical quantities and are merely convenient labels applied to these quantities.

The computing device 700 may include other components that are not shown nor further discussed herein for the sake of brevity. One having ordinary skill in the art will understand any hardware and software that is included but not shown in FIG. 7. While embodiments have been described in the context of fully functioning computing devices, those skilled in the art will appreciate that the various embodiments are capable of being distributed as a program product in a variety of forms and that the disclosure applies equally, regardless of the particular type of machine or computer-readable media used to actually effect the embodiments.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by this disclosure. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The invention claimed is:

1. A method comprising:
launching a computer program that autonomously facilitates a conversation in which dialogue is exchanged with an individual to whom insulin is delivered,
wherein the conversation includes—
a first message, from the computer program, that requests the individual specify a value for a blood glucose level, and
a second message, from the individual, that specifies the value for the blood glucose level;
determining a dosage to treat the individual based on the value for the blood glucose level that is specified in the second message;
adjusting the dosage based on information regarding context of the individual; and
effecting delivery of an amount of insulin based on the dosage, as adjusted to account for the context of the individual.

2. The method of claim 1, wherein said launching is performed in accordance with a schedule that is set by a healthcare provider of the individual.

3. The method of claim 1, wherein said launching is performed in response to a determination that the individual has completed a predetermined activity.

4. The method of claim 3, further comprising:
receiving, via a wireless communication channel, data from a computing device that is located proximate to the individual; and
determining that the individual has completed the predetermined activity based on an analysis of the data.

5. The method of claim 1, wherein the information regarding the context of the individual is derived from the conversation.

6. A method comprising:
initiating a computer program that facilitates a conversation in which dialogue is exchanged with an individual to whom insulin is delivered,
wherein the conversation includes—
a first message, from the computer program, that requests the individual specify a value of a blood glucose level, and
a second message, from the individual, that specifies the value for the blood glucose level;
determining a dosage for treating the individual based on the value for the blood glucose level specified in the second message; and
effecting delivery of a suitable amount of insulin based on the dosage.

7. The method of claim 6, further comprising:
deriving information regarding a physical activity performed by the individual based on an analysis of the conversation; and
adjusting the dosage based on the information, so as to account for the physical activity performed by the individual.

8. The method of claim 6, further comprising:
deriving information regarding a food or a beverage consumed by the individual based on an analysis of the conversation; and
adjusting the dosage based on the information, so as to account for the food or the beverage consumed by the individual.

9. The method of claim 6, further comprising:
deriving information regarding a medication administered by the individual based on an analysis of the conversation; and
adjusting the dosage based on the information, so as to account for the medication administered by the individual.

10. The method of claim 6, further comprising:
acquiring, from a source external to the computer program, information regarding an external factor that affects, or is experienced by, the individual; and
adjusting the dosage based on the information, so as to account for the external factor.

11. The method of claim 10, wherein the external factor is daylight duration, average temperature, season, geographical altitude, or pollution level.

12. The method of claim 6, further comprising:
acquiring, from a source external to the computer program, information regarding a characteristic of the individual; and
adjusting the dosage based on the information, so as to account for the characteristic.

13. The method of claim 12, wherein the characteristic is age, gender, genotype, or phenotype.

14. The method of claim 6, wherein the dosage is a basal insulin dosage or a bolus insulin dosage.

15. The method of claim 6, wherein the computer program operates in accordance with a set of rules, at least one of which is customized for the individual to manage diabetes in a personalized manner.

16. A non-transitory medium with instructions that, when executed by a processor of a computing device, cause the computing device to perform operations comprising:
initiating a computer program that facilitates a conversation in which dialogue is exchanged with an individual to whom medication is delivered to manage a disease,
wherein the conversation includes—
a first message, from the computer program, that requests the individual specify a value for a physiological characteristic, and
a second message, from the individual, that specifies the value for the physiological characteristic;
deriving information regarding a physical activity that is performed by the individual based on an analysis of the conversation;
determining a dosage to treat the individual based on the value for the physiological characteristic specified in the second message;
adjusting the dosage based on the information, so as to account for the physical activity of the individual; and
effecting delivery of an amount of the medication based on the adjusted dosage.

17. The non-transitory medium of claim 16, wherein the operations further comprise:
posting, to an interface, the adjusted dosage for review by the individual.

18. The non-transitory medium of claim 16, wherein said effecting comprises:
generating an electronic signal that is configured to cause an insulin delivery device to administer insulin to the individual in accordance with the adjusted dosage.

19. The non-transitory medium of claim 18, wherein the insulin delivery device is configured to administer the insulin during the conversation.

20. The non-transitory medium of claim 18, wherein said effecting further comprises:
transmitting the electronic signal to the insulin delivery device via a network.

* * * * *